(12) United States Patent
Gan (10) Patent No.: US 10,877,053 B2
(45) Date of Patent: Dec. 29, 2020

(54) METHOD OF DETERMINING AN ANALYTE CONCENTRATION

(71) Applicant: Roche Diagnostics Operations, Inc., Indianapolis, IN (US)

(72) Inventor: Li Gan, Ebikon (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 153 days.

(21) Appl. No.: 15/911,948

(22) Filed: Mar. 5, 2018

(65) Prior Publication Data
US 2018/0259543 A1 Sep. 13, 2018

(30) Foreign Application Priority Data
Mar. 7, 2017 (EP) .................... 17159681

(51) Int. Cl.
| | |
|---|---|
| *G01N 33/96* | (2006.01) |
| *G01N 33/50* | (2006.01) |
| *G01N 27/333* | (2006.01) |
| *G01N 33/72* | (2006.01) |
| *G01N 27/327* | (2006.01) |

(Continued)

(52) U.S. Cl.
CPC .......... *G01N 33/96* (2013.01); *G01N 27/333* (2013.01); *G01N 33/50* (2013.01); *G01N 33/72* (2013.01); *G01N 27/3274* (2013.01); *G01N 27/4163* (2013.01); *G01N 27/4175* (2013.01)

(58) Field of Classification Search
CPC ............. G01N 27/3274; G01N 27/333; G01N 27/4163; G01N 27/4175; G01N 33/50; G01N 33/72; G01N 33/96; G01N 33/721; G01N 33/728; G01N 33/84; Y10T 436/10; Y10T 436/100833; Y10T 436/102499; Y10T 436/103332; Y10T 436/104998;
(Continued)

(56) References Cited

U.S. PATENT DOCUMENTS

| | | | |
|---|---|---|---|
| 5,112,455 A | 5/1992 | Cozzette et al. | |
| 5,204,264 A * | 4/1993 | Kaminer | G01N 35/00712 |
| | | | 436/19 |

(Continued)

FOREIGN PATENT DOCUMENTS

| | | |
|---|---|---|
| CN | 101430387 A | 5/2009 |
| CN | 103900938 A | 7/2014 |

(Continued)

*Primary Examiner* — Maureen Wallenhorst
(74) *Attorney, Agent, or Firm* — Roche Diagnostics Operations, Inc.

(57) ABSTRACT

A method of determining an analyte concentration in a sample by a sensor is disclosed. The method includes analyzing a sample signal generated by the sensor for an analyte being measured. If the sample signal is normal, the method includes comparing the sample signal with a first reference signal of a reference solution measured prior to measuring the sample in order to determine the analyte concentration. If the sample signal is abnormal, the method includes comparing the sample signal with a calculated reference signal point obtained by interpolation between the first reference signal and a second reference signal of the same reference solution measured after measuring the sample. Various methods of determining and handling errors based on signal patterns are also disclosed.

16 Claims, 8 Drawing Sheets

(51) Int. Cl.
G01N 27/417 (2006.01)
G01N 27/416 (2006.01)

(58) Field of Classification Search
CPC . Y10T 436/105831; Y10T 436/106664; Y10T 436/19
USPC .......... 436/8, 9, 11, 12, 14, 15, 16, 79, 124, 436/149, 150, 163, 164
See application file for complete search history.

(56) References Cited

U.S. PATENT DOCUMENTS

| | | | |
|---|---|---|---|
| 7,422,903 B2 * | 9/2008 | Conlon | G01N 33/4915 252/408.1 |
| 2003/0044318 A1 | 3/2003 | Olson | |
| 2008/0077330 A1 * | 3/2008 | Rauh | G01N 27/333 702/19 |
| 2013/0245401 A1 | 9/2013 | Estes et al. | |
| 2016/0054339 A1 * | 2/2016 | Ebrahim | G01N 33/78 435/4 |

FOREIGN PATENT DOCUMENTS

| | | |
|---|---|---|
| GB | 2457660 A | 8/2009 |
| WO | 2008/033073 A1 | 3/2008 |

* cited by examiner

METHOD OF DETERMINING AN ANALYTE CONCENTRATION

CROSS-REFERENCE TO RELATED APPLICATIONS

This application claims priority to European Patent Application No. 17159681.0, filed 7 Mar. 2017, the disclosure of which is hereby incorporated by reference in its entirety.

TECHNICAL FIELD

This disclosure relates to a more accurate method of measuring an analyte concentration in a sample by a sensor.

BACKGROUND

In medicine, a doctor's diagnosis and patient treatment often relies on the measurement of the concentration of analytes or other parameters in a patient sample. This measurement is typically carried out by in-vitro diagnostic instruments that can be configured to analyze certain types of samples and detect certain types of analytes using various detecting technologies. As the life of patients may depend on the precision and the reliability of such measurements it is important that the instruments perform correctly.

It is a general requirement for in-vitro diagnostic systems to implement a set of Quality Control (QC) procedures to check that the instruments are working correctly.

One of these procedures is calibration. In most cases calibration is performed using standard solutions, with known concentrations. In this way it is possible to correlate a measured signal to a quantitative result. Calibration should be performed more or less frequently depending on the system and other variable factors that may affect performance.

In addition, between consecutive calibrations, one or more reference samples, also called QC samples, with known values of the analytes or parameters of interest are typically also measured, in the same way as test samples are measured, in order to further check that the calibrated instrument is actually within the specifications or admissible range.

However, even after correct calibration and validation with QC samples, detectors and sensors used to measure analyte concentrations can be subject to interferences, e.g., due to presence and/or high concentration of interfering substances in a particular test sample, and can be subject to temporary signal instability. In particular, some sensors may experience a signal drift that in some cases may remain unnoticed. This can lead to measurement errors.

Also, it is possible that signal drift occurs during calibration or measurement of QC samples.

In most cases an error occurred during calibration or a quality control is reported as a calibration failure or as a QC failure. Even in such cases, however, it is not always clear what the cause of the failure is. The failure may be due to a malfunctioning sensor but could be also due to other malfunctioning parts or interferences within the instrument, e.g., presence of air bubbles, clogging, contamination or mechanical failures.

If the cause cannot be determined, this may lead to wrong assumptions and false decisions when trying to resolve the issue. For example, a user may decide to replace a sensor whereas the cause of the error is to be found in another part of the instrument, thus resulting in increased costs and instrument down times.

SUMMARY

It is against the above background that the present disclosure provides certain unobvious advantages and advancements over the prior art. In particular, the inventors have recognized a need for improvements in methods for determining an analyte concentration.

Although the embodiments of the present disclosure are not limited to specific advantages or functionality, it is noted that the present disclosure provides a new method that enables to greatly reduce measurement errors. This is achieved by analyzing the sample signal and, based on the signal pattern, applying corrective measures, therefore increasing accuracy and reliability in determining concentrations of analytes in a sample. The present disclosure further enables to discriminate sensor errors from other types of errors and to trigger additional actions that facilitate troubleshooting, reduce maintenance and service costs, accelerate complaint handling and minimize instrument down times.

In accordance with one embodiment of the present disclosure, a method of determining an analyte concentration in a sample by a sensor is provided, the method comprising analyzing a sample signal for an analyte being measured and if the sample signal is normal, that is if it remains within an expected or predefined range and/or if it follows an expected trend over a predefined measurement time, the method comprises comparing the sample signal with a first reference signal of a reference solution measured prior to measuring the sample in order to determine the analyte concentration, and if the sample signal is abnormal, that is if it falls at least in part out of the expected or pre-defined range and/or if it drifts beyond a predefined threshold over a predefined measurement time, the method comprises comparing the sample signal with a calculated reference signal point obtained by interpolation between the first reference signal and a second reference signal of the same reference solution measured after measuring the sample.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Skilled artisans appreciate that elements in the figures are illustrated for simplicity and clarity and have not necessarily been drawn to scale. For example, dimensions of some of the elements in the figures may be exaggerated relative to other elements to help improve understanding of the embodiment(s) of the present disclosure.

DETAILED DESCRIPTION

A method of determining an analyte concentration in a sample by a sensor is disclosed. The method comprises analyzing a sample signal generated by the sensor for an analyte being measured. If the sample signal is normal, the method comprises comparing the sample signal with a first reference signal of a reference solution measured prior to measuring the sample in order to determine the analyte concentration. If the sample signal is abnormal, the method comprises comparing the sample signal with a calculated reference signal point obtained by interpolation between the first reference signal and a second reference signal of the same reference solution measured after measuring the sample.

The term "sample" is herein generally used to indicate either a test sample or a QC sample or a calibrator.

The term "test sample" refers to a biological material suspected of containing one or more analytes of interest and whose detection, qualitative and/or quantitative, may be associated to a clinical condition. The test sample can be derived from any biological source, such as a physiological fluid, including blood, saliva, ocular lens fluid, cerebral spinal fluid, sweat, urine, milk, ascites fluid, mucous, synovial fluid, peritoneal fluid, amniotic fluid, tissue, cells or the like. The test sample can be pretreated prior to use, such as preparing plasma from blood, diluting viscous fluids, lysis or the like; methods of treatment can involve filtration, centrifugation, distillation, concentration, inactivation of interfering components, and the addition of reagents. A test sample may be used directly as obtained from the source in some cases or following a pretreatment and/or sample preparation workflow to modify the character of the sample, e.g., after adding an internal standard, after being diluted with another solution or after having being mixed with reagents, e.g., to enable carrying out one or more in vitro diagnostic tests, or for enriching (extracting/separating/concentrating) analytes of interest and/or for removing matrix components potentially interfering with the detection of the analyte(s) of interest.

According to an embodiment, the test sample is blood or a blood derivative such as plasma or serum. According to certain embodiments, analytes of interest are gases, such as $O_2$ and $CO_2$, blood electrolytes such as Sodium ($Na^+$), Potassium ($K^+$), Chloride ($Cl^-$), Calcium ($Ca^{++}$), protons ($H^+$) in relation to pH, metabolites such as Glucose and Lactate, drugs of abuse, therapeutic drugs, hormones, markers, proteins and the like. Other analytes of interest are hemoglobin, hemoglobin derivatives such as Deoxygenated hemoglobin, Oxyhemoglobin, Carboxyhemoglobin, Methemoglobin, and bilirubin. According to an embodiment a parameter of interest is hematocrit. The list is however not exhaustive.

The term "QC sample" refers to a reference sample, that mimics a test sample, and that contains known values of one or more QC substances. Typically, QC samples are supplied in one or more levels, e.g., two or three levels that correspond to different concentration ranges of the QC substances. QC samples are typically measured in the same way and under the same conditions as test samples are measured, in order to check that a calibrated sensor is actually within the specifications or admissible range.

A "QC substance" can be an analyte identical to an analyte of interest, the concentration of which is known, or that generates by reaction an analyte identical to an analyte of interest, the concentration of which is known, e.g., $CO_2$ from bicarbonate, or it can be any other equivalent substance of known concentration, which mimics the analyte of interest or that can be otherwise correlated to a certain parameter of interest, e.g., a dye that behaves optically similar to hemoglobin or bilirubin.

A "calibrator" is a calibration solution that contains known values of one or more calibration materials used for calibration and that is measured under the same conditions as a sample. In particular, a calibrator can be measured like a test sample or a QC sample between a first reference solution measurement and a second reference solution measurement. Typically, one or two calibrators are used for a one-point or two-point calibration respectively, when the sensor responds linearly to analyte concentrations. Three or more calibrators may be used if the calibration curve is non-linear. In particular, also calibrators can be provided in different levels that correspond to different concentration ranges of the QC materials.

A calibration material can be the same as a QC substance.

A "reference solution" is a standard solution such as a calibrator, with known analyte concentration, that may be used for calibration, and that is routinely used for obtaining a reference measurement before and after a sample measurement.

According to an embodiment the reference solution is a standby solution. A "standby solution" is a solution that is used to rinse the sensor after a sample measurement and is kept in contact with the sensor until it is replaced by another sample.

The term "sensor" is herein generically used to indicate a detector configured to respond to changes of analyte concentration in a sample and generate a correlated signal output that can be quantified and digitized. The sensor can be a biosensor, a chemical sensor or a physical sensor. Also, the sensor can be selective or even specific with respect to one analyte of interest in a sample or can be configured to detect and quantify a plurality of different analytes of interest.

The sensor is typically part of a larger in-vitro diagnostic system. An "in-vitro diagnostic system" is a laboratory automated or semi-automated system dedicated to the analysis of samples for in vitro diagnostics. The in-vitro diagnostic system may have different configurations according to the need and/or according to the desired laboratory workflow. The in-vitro diagnostic system can comprise one or more analytical instruments, comprising at least one detector or sensor, designed to execute respective workflows that are optimized for one or more certain types of analysis, and to detect certain types of parameters, e.g., gases, electrolytes, metabolites, clinical chemistry analytes, immunochemistry analytes, coagulation parameters, hematology parameters, etc. Thus the in-vitro diagnostic system may comprise one analytical instrument or a combination of any of such analytical instruments with respective workflows and respective detectors, where pre-analytical and/or post analytical modules may be coupled to individual analytical instruments or be shared by a plurality of analytical instruments. In alternative pre-analytical and/or post-analytical functions may be performed by units integrated in an analytical instrument. The in-vitro diagnostic system can comprise functional units such as liquid handling units for pipetting and/or pumping and/or mixing of samples and/or reagents and/or system fluids, and also functional units for sorting, storing, transporting, identifying, separating, detecting.

According to an embodiment the in-vitro diagnostic system comprises an analytical instrument with at least one sensor.

According to an embodiment, the sensor may comprise a plurality of sensor zones, e.g., arranged in a flow-through sensoric path, each sensor zone being configured to be specific or selective with respect to one analyte of interest.

According to an embodiment, the sensor is configured for detecting and quantifying any one or more of a gas, an electrolyte, a metabolite.

According to certain embodiments, the sensor is based on the potentiometric, amperometric, conductometric, or optical measurement principle.

According to an embodiment, the sensor is an ion-selective electrode (ISE) sensor and the sample signal is a potentiometric signal.

According to an embodiment, the analyte is any of a proton, chloride ion, sodium ion, potassium ion, calcium ion.

According to certain embodiments the sensor is a pH sensor or an ISE sensor for determining electrolyte values such as $Na^+$, $K^+$, $Ca^{2+}$ and $Cl^-$.

A pH sensor typically comprises a pH-sensitive membrane. Depending on the pH value of the test sample, electric potential is generated at the boundary layer between the membrane and the sample. This potential can be measured potentiometrically by a reference sensor.

Also $Na^+$, $K^+$, $Ca^{2+}$ and $Cl^-$ ISE sensors typically work according to the potentiometric measuring principle. They differ only by different membrane materials that enable sensitivity for the respective electrolytes.

A "sample signal" is the signal output generated by the sensor when measuring an analyte concentration in a test sample, QC sample or calibrator.

A "reference signal" is the signal output generated by the sensor when measuring a reference solution and in particular an analyte concentration in the reference solution before and/or after measuring a sample.

A signal may be a continuous signal over a period of time or it may refer to a single measurement point or a plurality of discrete measurement points over time, to form a signal pattern.

A "signal pattern" refers to the signal behavior over time either with respect to a continuous signal or to a plurality of measurement points over time.

A signal or signal pattern, i.e., either a sample signal or reference signal, is "normal" if the signal remains within an expected or predefined range and/or if it follows an expected trend over a limited measurement time.

A signal or signal pattern, i.e., either a sample signal or reference signal, is "abnormal" whenever it deviates from normal behavior and in particular if it falls at least in part out of the expected or pre-defined range and/or if it shows a significant signal drift, i.e., if the signal drifts beyond a predefined threshold, over a limited measurement time.

The limited measurement time can be any predefined time, but typically less than a minute, e.g., about 30 seconds.

According to an embodiment, a signal or signal pattern, i.e., either a sample signal or reference signal, is normal if the normalized measurement points of the signal are of the same sign and it is abnormal if the normalized measurement points of the signal have at least in part opposite sign.

If the sample signal is normal, the method comprises comparing the sample signal with a first reference signal of a reference solution measured prior to measuring the sample in order to determine the analyte concentration. More specifically, the method comprises comparing at least one measurement point of the sample signal with at least one measurement point of a first reference signal of a reference solution measured prior to measuring the sample. This corresponds to one-point calibration with the reference solution being measured before measuring the sample in order to generate a first reference signal and calculate the analyte concentration in the sample.

According to an embodiment, the first reference signal is the last available measurement point or a projected (extrapolated) measurement point of the measured reference solution. The at least one measurement point of the first reference signal may be however another measurement point such as one of the last few measurement points, a minimum point or a maximum point or an average of a plurality of measurement points measured over time.

If the sample signal is abnormal, the method comprises comparing the sample signal with a calculated reference signal point obtained by interpolation between the first reference signal and a second reference signal of the same reference solution measured after measuring the sample. More specifically, the method comprises comparing at least one measurement point of the sample signal with a calculated reference signal point obtained by interpolation between the at least one measurement point of the first reference signal and at least one measurement point of a second reference signal of the same reference solution measured after measuring the sample. This means measuring the same reference solution before and after measuring the sample in order to generate a first reference signal and a second reference signal respectively, both of which are taken into account for calculating the analyte concentration. This is because the second reference signal can be different from the first reference signal, especially if a signal drift occurs during sample measurement, and taking only the first reference signal or only the second reference signal into account is less accurate. This corresponds to one-point calibration, however with respect to a calculated (interpolated) reference value by measuring the same reference solution before and after measuring a sample.

It can be advantageous to use a standby solution as the reference solution to be measured before and after sample measurement as the standby solution can be used to rinse the sensor and contact the sensor between different samples and its signal can be therefore detected in proximity of each sample measurement, including before and after each sample measurement.

According to one embodiment the at least one measurement point of the second reference signal is the first available measurement point of the second reference signal. The at least one measurement point of the second reference signal may be however another measurement point such as one of the first few measurement points, a minimum point or a maximum point or an average of a plurality of measurement points.

According to one embodiment the at least one measurement point of the sample signal is the last available measurement point of the sample signal or a projected (extrapolated) point of the sample signal. The at least one measurement point of the sample signal may be however another measurement point such as one of the last few measurement points, a minimum point or a maximum point or an average of a plurality of measurement points.

According to one embodiment, if the sample signal is abnormal, the method comprises flagging the sample measurement and/or indicating that the analyte concentration is an interpolated analyte concentration.

According to one embodiment, if the sample signal is repeatedly abnormal for consecutive sample measurements, e.g., for a predetermined number of times, where the sample can be the same sample or different samples, the method comprises indicating a sensor error.

According to one embodiment where the sample is a QC sample and the sample signal, the first reference signal and the second reference signal are normal and a QC failure occurs, the method comprises repeating measurement of the QC sample and/or indicating an error other than a sensor error.

According to one embodiment where the sample is a QC sample and any one or more of the sample signal, the first reference signal and the second reference signal are abnormal and a QC failure occurs a pre-defined number of times, the method comprises indicating a sensor error. The method may include attempting to resolve the cause of the sensor error before indicating a sensor error.

According to one embodiment where the sample is a calibrator and the sample signal, the first reference signal and the second reference signal are normal and a calibration failure occurs, the method comprises repeating measurement of the calibrator and/or indicating an error other than a sensor error.

According to one embodiment where the sample is a calibrator and where any one or more of the sample signal, the first reference signal and the second reference signal are abnormal and a calibration failure occurs a pre-defined number of times, the method comprises indicating a sensor error. The method may include attempting to resolve the cause of the sensor error before indicating a sensor error.

According to one embodiment, the method comprises saving, at least temporarily, any signal and/or any error in a database and/or trouble shooting report of an analytical instrument.

According to one embodiment, the method comprises transmitting and collecting any signal and/or any error from one or more local analytical instruments to a remote server or cloud for monitoring instrument and/or sensor performance, and/or for analyzing data to improve instrument and/or sensor performance and/or for facilitating service or trouble shooting and/or for remotely triggering corrective actions or other types of actions.

Other and further objects, features and advantages will appear from the following description of exemplary embodiments and accompanying drawings, which serve to explain the principles more in detail.

Figure 1:
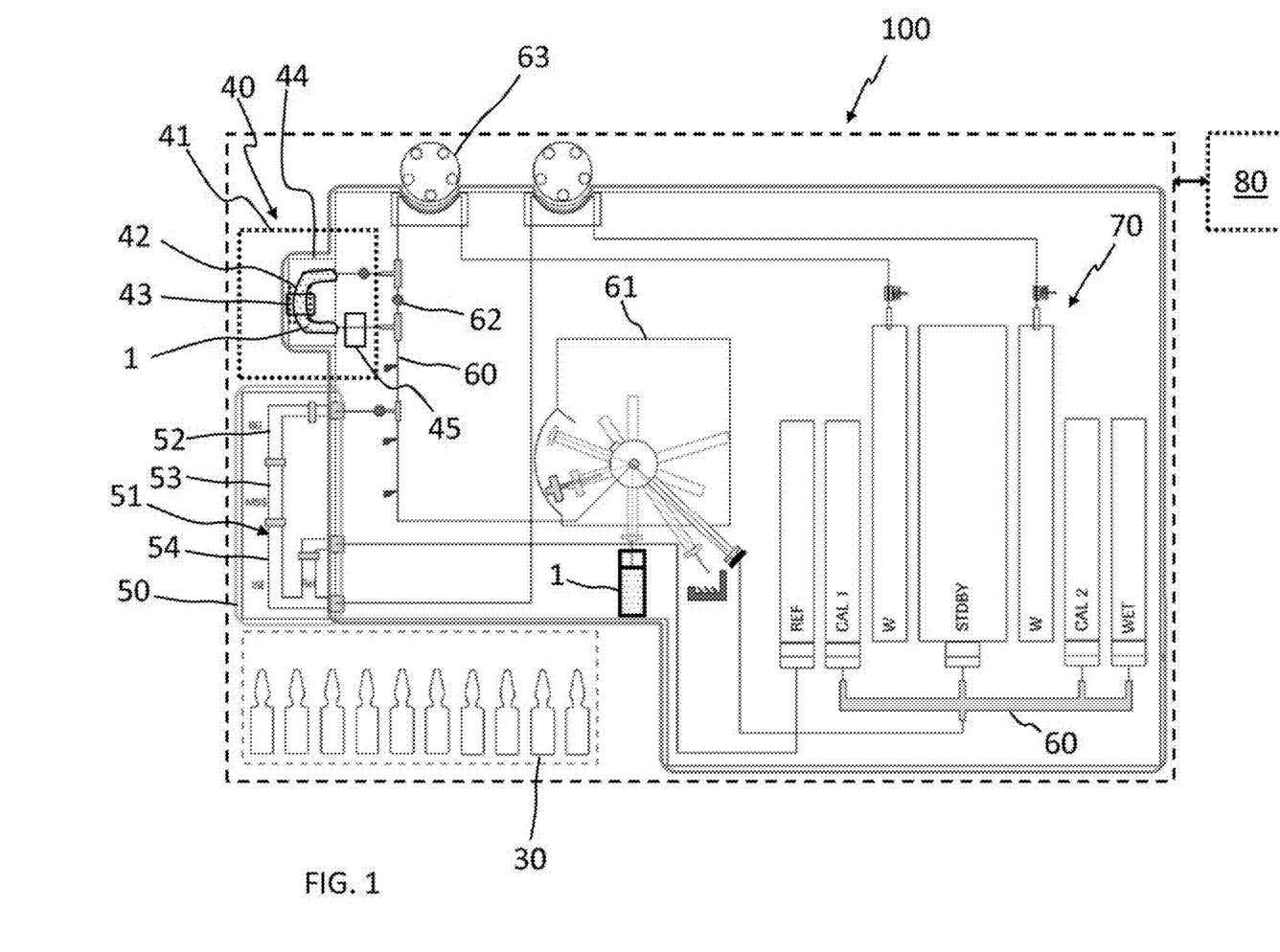
FIG. 1 shows an example of an analytical instrument and sensor comprised therein in accordance with an embodiment of the present disclosure.

FIG. 1 shows schematically an example of an analytical instrument 100. The analytical instrument 100 comprises a first detector 40 and a second detector 50 for detecting respective parameters of a test sample 1.

The first detector 40 comprises an optical unit 41 and in particular an oximetry unit for photometrically detecting any one or more of hemoglobin, including derivatives of hemoglobin, and bilirubin. In particular, the optical or oximetry unit 41 comprises a light source 42, an optical sensor 43 such as a photodiode array, a sample cuvette 44 arranged between the light source 42 and the optical sensor 43 and optical elements such as lenses and a polychromator (not shown), for guiding light from the light source 42 to a test sample 1 in the cuvette 44 and from the test sample 1 to the optical sensor 43 for measuring an absorbance spectrum.

The second detector 50 is embodied as a plug-in cartridge comprising a flow-through sensoric path 51, comprising a gas sensoric zone 52 comprising a PO2 sensor, a PCO2 sensor and a pH sensor, a metabolite sensoric zone 53, comprising a glucose sensor and a lactate sensor, and an electrolyte sensoric zone 54, comprising ISE sensors for detecting respectively $Na^+$, $K^+$, $Ca^{2+}$, and $Cl^-$.

The analytical instrument 100 further comprises fluidic lines 60, a fluid injector 61, valves 62 and pumps 63 for moving fluids through the fluidic lines 60 and in particular in and out of the cuvette 44 of the first detector 40 and/or through the sensoric path 51 of the second detector 50, where respective analytes can be determined.

The analytical instrument 100 further comprises a fluid package 70 comprising fluid reservoirs, including a reference solution (REF), a first calibrator (Cal 1), a second calibrator (Cal 2), a standby solution (STDBY), a wetting fluid (WET) and two waste containers (W). The wetting fluid (WET) is used every time a new cartridge or detector 50 is plugged for conditioning the new cartridge 50.

The $Na^+$, $K^+$, $Ca^{2+}$, $Cl^-$, pH and CO2 parameters are calibrated using the STDBY and Cal 2 solutions, which contain a defined quantity of electrolytes and acidic or alkaline components of a pH buffer system. By ensuring airtight access to the calibration solutions, the CO2 content can be kept steady and then used as a basis for calibration.

The CAL 2 solution contains a very low concentration of oxygen and thus is used to calibrate the low calibration point in a two-point calibration. The high calibration point is calibrated using the standby solution. The oxygen concentration of the standby solution corresponds to that of the ambient air.

For the glucose/lactate sensors, due to the non-linear nature of the calibration curve, three calibration points are determined. The STDBY, Cal 1 and Cal 2 solutions are used for this purpose.

Calibrating the oximetry unit 41 requires wavelength calibration of the polychromator and layer thickness calibration of the cuvette 44. For this purpose, the optical unit 41 comprises a second light source (not shown), which is a neon lamp. The neon lamp is a gas discharge light, which emits only certain defined wavelengths. The peaks in the neon emission spectrum are used to calibrate the wavelength scale. The layer thickness of the cuvette 44 is calibrated using the Cal 2 solution, which contains a dye for this purpose.

The standby solution STDBY is also used for rinsing the fluidic lines 60, the flow-through path 51 and the cuvette 44.

The analytical instrument 100 further comprises QC samples 30, supplied in three levels of respective concentration ranges for each parameter. In particular, the QC samples 30 comprise QC substances in different concentrations for different levels, which are required for performing the QC procedure with respect to both the first detector 40 and the second detector 50.

The analytical instrument 100 further comprises a controller 80 configured to determine an analyte concentration, e.g., in a test sample 1 or QC sample 30 or calibrator, e.g., Cal 2. In particular, the controller 80 is configured to analyze a sample signal generated, e.g., by any of the sensors in the second detector 50, e.g., any of the ISE sensors of the electrolyte sensoric zone 54, for a respective analyte being measured, and judging if the sample signal is normal or abnormal. If the sample signal is normal, the controller 80 is configured to compare the sample signal with a first reference signal obtained by measuring the standby solution STDBY as reference solution prior to measuring the sample 1, 30 in order to determine the analyte concentration. If the sample signal is abnormal, the controller 80 is configured to compare the sample signal with a calculated reference signal point obtained by interpolation between the first reference signal and a second reference signal of the same standby solution STDBY measured after measuring the sample 1, 30 or Cal 2.

Figure 2:
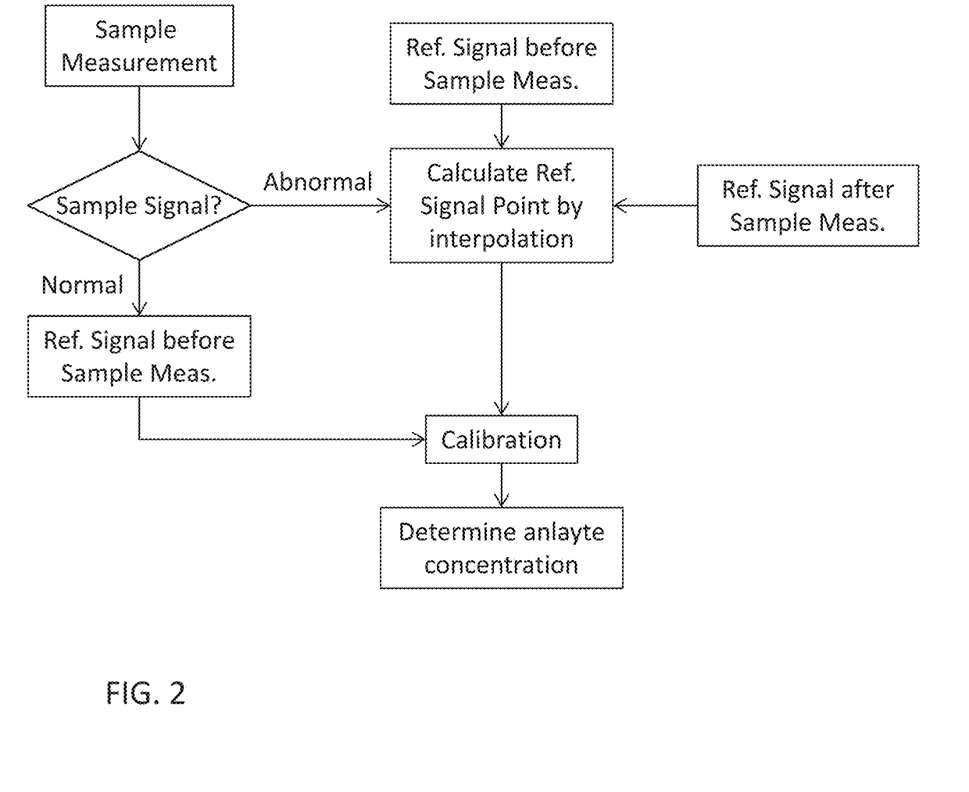
FIG. 2 generally depicts a method of determining an analyte concentration in a sample by a sensor in accordance with an embodiment of the present disclosure.

In the flow diagram of FIG. 2, a method of determining an analyte concentration in a sample by a sensor is illustrated. The method comprises measuring a sample and analyzing the sample signal for an analyte being measured. If the sample signal is normal, the method comprises comparing the sample signal with a first reference signal of a reference solution measured prior to measuring the sample, thus performing a calibration based on such first reference signal, in order to determine the analyte concentration. If the sample signal is abnormal, the method comprises calculating a reference signal point by interpolation between the first reference signal and a second reference signal of the same reference solution measured after measuring the sample, and comparing the sample signal with the calculated reference signal point, thus performing a calibration based on such calculated reference signal point, in order to determine the analyte concentration.

Figure 3:
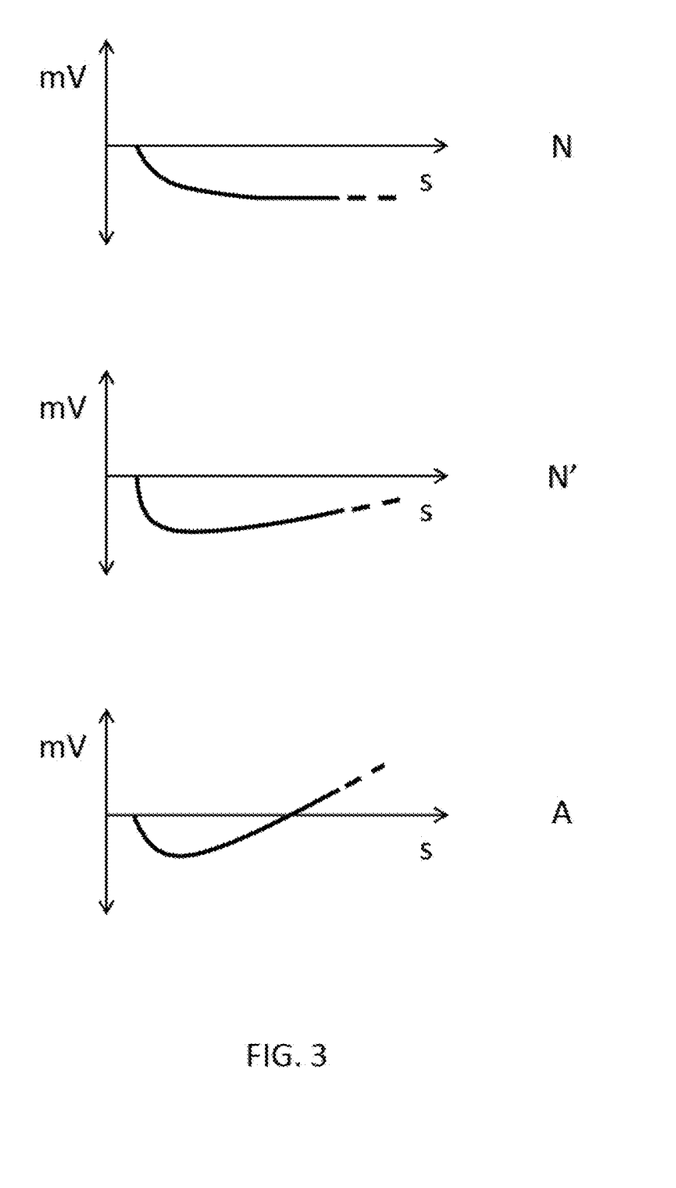
FIG. 3 schematically shows three examples of sample signal in accordance with an embodiment of the present disclosure.

FIG. 3 schematically shows three examples of normalized sample signals generated by an ISE sensor, although other types of sample signal are also possible and may be different for different types of sensor. The sample signals are measured in electrical potential (mV) versus time in seconds (s). The first sample signal on the top of FIG. 3 has a typical pattern where the electrical potential keeps decreasing over time until stabilizing. This is an example of normal sample signal or signal pattern N. With respect to the second sample signal in FIG. 3, the electrical potential tends to slowly increase again after decreasing, however still remaining negative over the measurement time, i.e., the normalized measurement points of the sample signal are of the same sign. This sample signal can be considered still in an acceptable normal range N'. With respect to the third sample signal at the bottom of FIG. 3, a clear signal drift can be observed. In particular, the electrical potential decreases in a first phase before significantly increasing again and passing from negative to positive sign, i.e., the normalized measurement points have in part opposite sign. In this case the sample signal is abnormal A.

Figure 4:
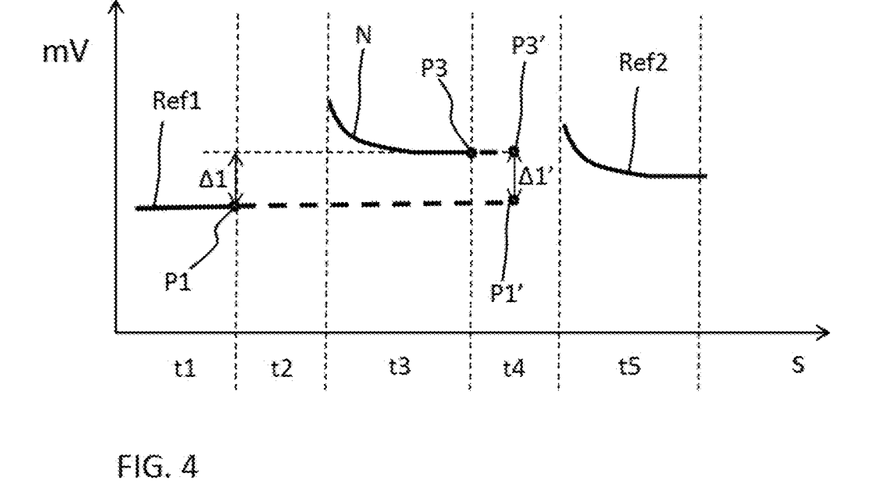
FIG. 4 depicts a method of determining an analyte concentration when the sample signal is normal in accordance with an embodiment of the present disclosure.

FIG. 4 shows in more detail a method of determining an analyte concentration when the sample signal is normal N. In the graph of FIG. 4, where electrical potential in mV is plotted versus time in seconds (s), a sample signal N between a first reference signal Ref1 and a second reference signal Ref2 are shown. The sample signal N is generated during a measurement time window t3. The first reference signal Ref1 and the second reference signal Ref2 are generated by measuring the same reference solution before and after measuring the sample in a time window t1 and t5 respectively. The time window t2 between t1 and t3 is the time during which the reference solution is removed from the sensor and it is replaced by the sample. The time window t4 between t3 and t5 is the time during which the sample is removed from the sensor and it is replaced by the reference solution. Advantageously the reference solution is the same standby solution SDTBY that is used also to rinse the sensor and is kept in contact with the sensor until a sample is introduced.

In this case, where the sample signal is normal N, the method comprises comparing the sample signal N with the first reference signal Ref1 in order to determine the analyte concentration. In particular, a measurement point P3 or a projected point P3' of the sample signal N, and a measurement point P1 or a projected point P1' of the first reference signal Ref1 respectively may be chosen when comparing the sample signal N with the first reference signal Ref1. In this example, P3 is the last available measurement point of the sample signal N and P1 is the last available measurement point of the first reference signal Ref1. The difference $\Delta 1$ between P3 and P1 or the difference $\Delta 1'$ between P3' and P1' may be used to determine the analyte concentration in the sample, where $\Delta 1$ and $\Delta 1'$ provide comparable results. The second reference signal Ref2 is not taken into account. It is noted that whereas the sample signal is normal N, and despite the same reference solution is measured before and after measuring the sample the second reference signal Ref2 can be different from the first reference signal Ref1 or offset with respect to the first reference signal Ref1.

Figure 5:
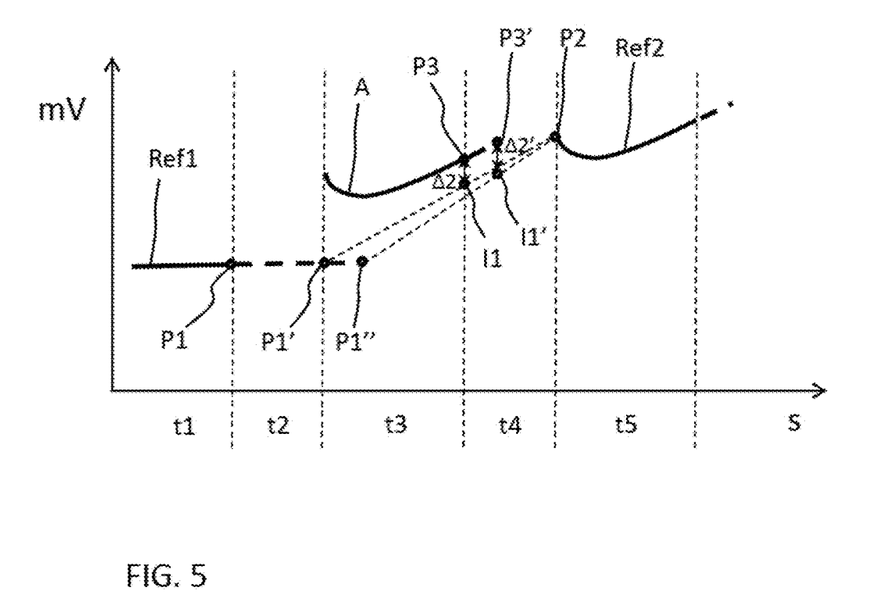
FIG. 5 depicts a method of determining an analyte concentration when the sample signal is abnormal in accordance with an embodiment of the present disclosure.

FIG. 5 shows in more detail a method of determining an analyte concentration when the sample signal is abnormal A. Analogously to FIG. 4, the sample signal A is shown between a first reference signal Ref1 and a second reference signal Ref2, where also in this case Ref1 and Ref2 are obtained by measuring the same reference solution, and in particular the same standby solution SDTBY before and after measuring the sample. The time windows t1-t5 are the same as for FIG. 4. However, in this case, where the sample signal is abnormal A, the second reference signal Ref2 is taken into account. In particular, the method comprises comparing the sample signal with a calculated reference signal point I1, I1' obtained by interpolation between the first reference signal Ref1 and the second reference signal Ref2.

In this example a projected point P1', P1" of the first reference signal Ref1 and a measurement point P2 of the second reference signal Ref2 respectively are chosen for obtaining a calculated reference signal point I1, I1' in correspondence to a measurement point P3 or projected measurement point P3' of the sample signal A. In this example, P3 is the last available measurement point of the sample signal A, P2 is the first measurement point of the second reference signal Ref2, P1' is a projected point of the first reference signal Ref1 in correspondence to the first measurement point of the sample signal A and P1" is a projected point of the first reference signal Ref1 in correspondence to the measurement point with minimum value of the sample signal A. The difference $\Delta 2$ between P3 and I1 or the difference $\Delta 2'$ between P3' and I1' may be used to determine the analyte concentration in the sample, where $\Delta 2$ and $\Delta 2'$ provide comparable results.

It is noted that both the sample signal pattern A and the second reference signal Ref2 have an abnormal pattern meaning that an error may have occurred already during sample measurement. In this case using both the first reference signal Ref1 and the second reference signal Ref2 contributes to compensate for any eventual error and to determine a more accurate analyte concentration.

Figure 6:
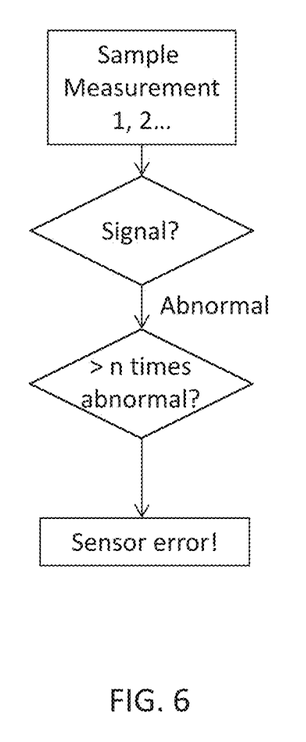
FIG. 6 depicts a method of determining an error in accordance with an embodiment of the present disclosure.

FIG. 6 depicts a method of determining an error. In particular, if the sample signal pattern is repeatedly abnormal for consecutive sample measurements, i.e., for more than a pre-defined number of times n, where n can be any number including 1, the method comprises indicating a sensor error.

Figure 7:
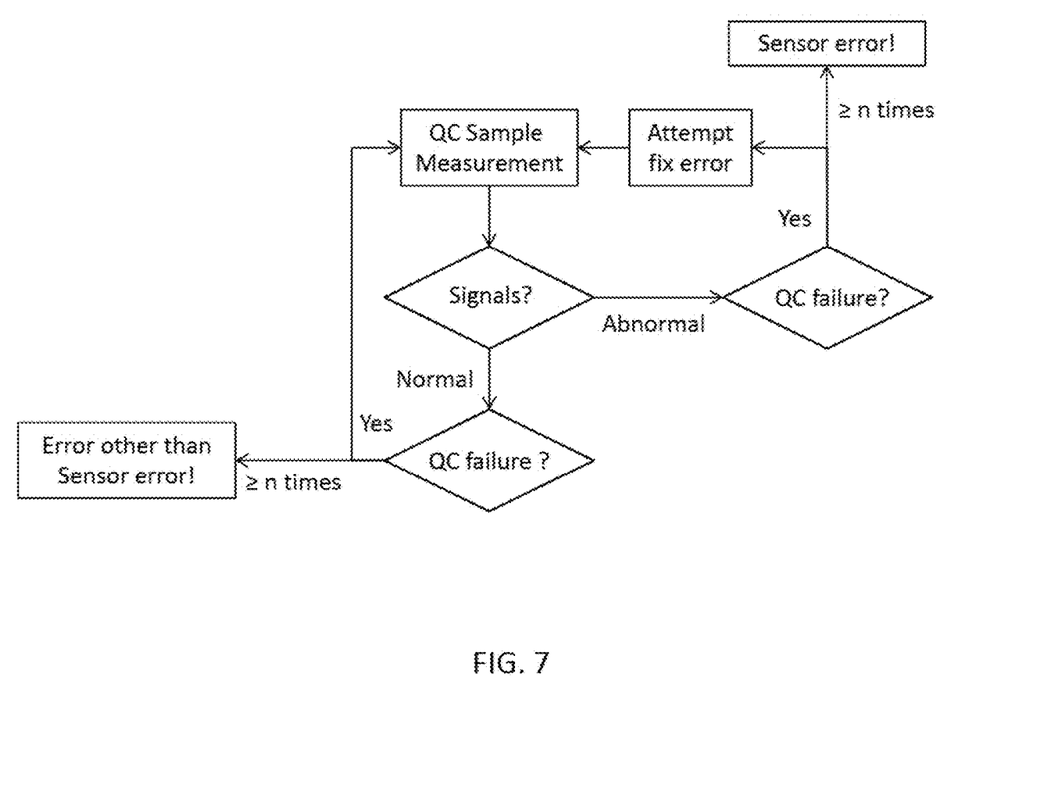
FIG. 7 depicts another method of determining an error in accordance with an embodiment of the present disclosure.

FIG. 7 depicts another method of determining an error. In particular, if the sample is a QC sample and a QC failure occurs despite the signal patterns, including the sample signal pattern and the reference signal patterns, are normal, the method comprises repeating measurement of the QC sample and/or indicating an error other than a sensor error. In particular, the error other than a sensor error may be indicated after measurement of the QC sample n times, where n can be any number including 1, and obtaining a QC failure despite normal signal patterns. On the other hand, if a QC failure occurs and in addition any one or more of the signal patterns, including the sample signal pattern and the reference signal patterns, are abnormal the method comprises indicating a sensor error, after eventually attempting to resolve the cause of the error. In particular, the sensor error may be indicated after measurement of the QC sample n times, where n can be any number including 1, and after failing to fix the error.

Figure 8:
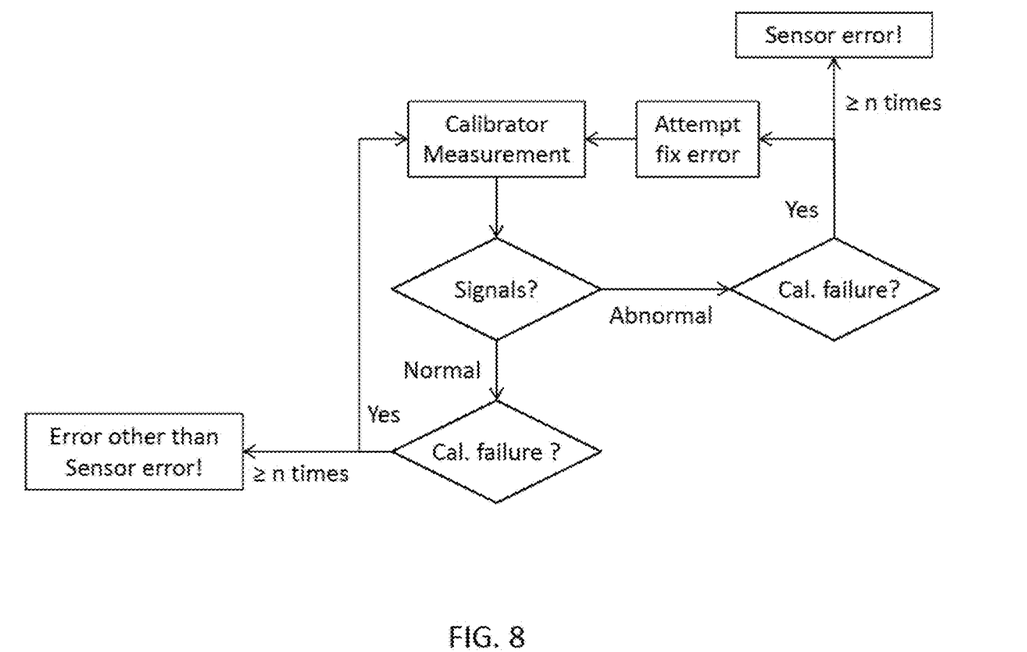
FIG. 8 depicts another method of determining an error in accordance with an embodiment of the present disclosure.

FIG. 8 depicts another method of determining an error. In particular, if the sample is a calibrator, e.g., CAL 2, and a calibration failure occurs despite the signal patterns, including the sample signal pattern and the reference signal patterns are normal, the method comprises repeating measurement of the calibrator and/or indicating an error other than a sensor error. In particular, the error other than a sensor error may be indicated after measurement of the calibrator n times, where n can be any number including 1, and obtaining a calibration failure despite normal signal patterns. On the other hand, if a calibration failure occurs and in addition any one or more of the signal patterns, including the sample signal pattern and the reference signal patterns, are judged to be abnormal the method comprises indicating a sensor error, after eventually attempting to resolve the cause of the error. In particular, the sensor error may be indicated after measurement of the calibrator n times, where n can be any number including 1, and after failing to fix the error.

Figure 9:
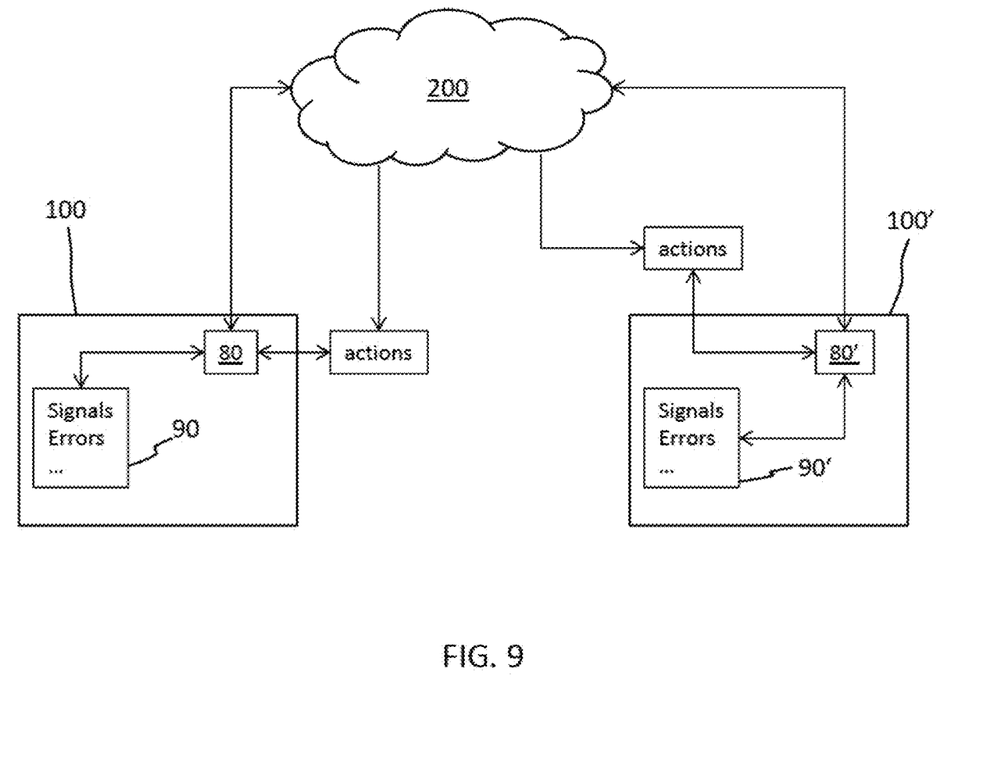
FIG. 9 depicts a method of handling signals and errors in accordance with an embodiment of the present disclosure.

FIG. 9 depicts a method of handling signals and errors among other possible data. The method comprises saving, at least temporarily, signal patterns and/or any error in a database and/or trouble shooting report 90, 90' of an analytical instrument 100, 100'.

The method comprises transmitting and collecting any signal and/or any error from one or more local analytical instruments 100, 100' to a remote server or cloud 200 for monitoring instrument and/or sensor performance, and/or for analyzing data to improve instrument and/or sensor performance and/or for facilitating service or trouble shooting and/or for remotely triggering corrective actions or other types of actions. Actions may be triggered also locally at instrument level via communication between the database 90, 90' and the controller 80, 80'.

The remotely collected data may be used for example for updating the method (algorithm) of determining analyte concentration, e.g., by adapting the range or threshold that defines when a signal is normal or abnormal, or the requirements for indicating a sensor error, e.g., by changing the number of times a QC failure and/or a calibration failure and/or an abnormal signal has to occur before indicating an error and/or for updating or adding procedures for resolving causes of errors.

The collected data may be also used for proactive customer service, e.g., to inform a user and provide a new sensor when a sensor error is recognized and/or automatically schedule a field service when another malfunctioning requiring a field service engineer is recognized.

Also, based on a user behavior, e.g., usage/measurement frequency, it is possible to automatically reserve an adequate amount of sensors for each user, or suggest a more suitable sensor version for each user, e.g., a sensor optimized for higher throughput but with shorter lifetime or optimized for longer lifetime but lower throughput.

Thus, issue tracking, complaint handling and customer care in general can be facilitated.

Modifications and variations of the disclosed embodiments are certainly possible in light of the above description. It is therefore to be understood, that within the scope of the appended claims, the embodiments may be practiced otherwise than as specifically devised in the above examples.

It is noted that terms like "preferably," "commonly" and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

For purposes of describing and defining the subject matter of the present disclosure it is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various modifications and variations can be made to the embodiments described herein without departing from the spirit and scope of the claimed subject matter. Thus, it is intended that the specification cover the modifications and variations of the various embodiments described herein, provided such modifications and variations come within the scope of the appended claims and their equivalents.

What is claimed is:

1. A method of determining an analyte concentration in a sample, the method comprising:
   measuring said analyte concentration in said sample using a sensor,
   obtaining an abnormal sample signal, and
   comparing the abnormal sample signal with a calculated reference signal point obtained by interpolation between a first reference signal of a reference solution measured prior to measuring the sample, and a second reference signal of the same reference solution measured after measuring the sample in order to determine a corrected analyte concentration in the sample.

2. The method of claim 1, wherein the reference solution is a standby solution.

3. The method of claim 1, wherein the first reference signal is comprised of multiple measurement points, and the first reference signal is a last available measurement point of the first reference signal or a projected point of the first reference signal.

4. The method of claim 1, wherein the second reference signal is comprised of multiple measurement points, and the second reference signal is a first available measurement point of the second reference signal.

5. The method of claim 1, wherein the sample signal is comprised of multiple measurement points, and the sample signal is a last available measurement point of the sample signal or a projected point of the sample signal.

6. The method of claim 1 further comprising obtaining normalized measurement points of the sample signal or the reference signals, wherein the sample signal or reference signals are normal if the normalized measurement points of the sample signal or reference signals respectively are of the same sign and wherein the sample signal or reference signals are abnormal if the normalized measurement points of the sample signal or reference signals respectively have at least in part opposite sign.

7. The method of claim 1, wherein the sensor is an ion-selective electrode sensor and the sample signal is a potentiometric signal.

8. The method of claim 1, wherein the analyte is a proton, chloride ion, sodium ion, potassium ion, or calcium ion.

9. The method of claim 1, wherein if the sample signal is repeatedly abnormal for consecutive sample measurements, the method comprises indicating a sensor error.

10. The method of claim 1, wherein the sample is a quality control sample and wherein if the sample signal, the first reference signal and the second reference signal are normal and a quality control failure occurs, the method comprises repeating measurement of the quality control sample and/or indicating an error other than a sensor error.

11. The method of claim 10, wherein if any one or more of the sample signal, the first reference signal and the second reference signal are abnormal and a quality control failure occurs a pre-defined number of times, the method comprises indicating a sensor error.

12. The method of claim 1, wherein the sample is a calibrator and wherein if the sample signal, the first reference signal and the second reference signal are normal and a calibration failure occurs, the method comprises repeating measurement of the calibrator and/or indicating an error other than a sensor error.

13. The method of claim 12, wherein if any one or more of the sample signal, the first reference signal and the second reference signal are abnormal and a calibration failure occurs a pre-defined number of times, the method comprises indicating a sensor error.

14. The method of claim 1, wherein if the sample signal is repeatedly abnormal for consecutive sample measurements, indicating a sensor error.

15. The method of claim 14 further comprising saving any signal and/or any error in a database and/or trouble shooting report of an analytical instrument.

16. The method of claim 14 further comprising transmitting and collecting any signal and/or any error to a remote server or cloud for monitoring instrument and/or sensor performance, and/or for analyzing data to improve instrument and/or sensor performance and/or for facilitating service or trouble shooting and/or for remotely triggering corrective actions.

* * * * *